United States Patent [19]

Lazorthes et al.

[11] Patent Number: 4,738,267
[45] Date of Patent: Apr. 19, 1988

[54] IMPLANTABLE, INTRACRANIAL-PRESSURE SENSOR

[75] Inventors: Yves Lazorthes, Toulouse, France; Gil Clemente, Jaboatao Pernambuco, Brazil; Bernard Aragon, Castanet, France

[73] Assignee: Universite Paul Sabatier (Toulouse III), Toulouse, France

[21] Appl. No.: 845,782

[22] Filed: Mar. 24, 1986

[30] Foreign Application Priority Data

Mar. 22, 1985 [FR] France .................. 85 04448

[51] Int. Cl.$^4$ .......................................... A61B 5/00
[52] U.S. Cl. ........................... 128/748; 128/673
[58] Field of Search ........... 128/748, 673, 675, 715; 73/715

[56] References Cited

U.S. PATENT DOCUMENTS

| | | | |
|---|---|---|---|
| 2,510,073 | 6/1950 | Clark | 128/675 X |
| 3,943,915 | 3/1976 | Severson | 128/748 X |
| 4,147,161 | 4/1979 | Ikebe et al. | 128/748 |
| 4,191,193 | 3/1980 | Seo | 128/675 |
| 4,312,361 | 1/1982 | Nicholson et al. | 128/748 |
| 4,393,878 | 7/1983 | Kahn | 128/748 |

Primary Examiner—Kyle L. Howell
Assistant Examiner—Angela D. Sykes
Attorney, Agent, or Firm—Harold H. Dutton, Jr.

[57] ABSTRACT

The invention relates to a pressure sensor implanted into the skull to emit an electrical signal representing the intra-cranial pressure; this sensor is of the type which includes on one hand a test body (1) comprising a deforming diaphragm (3) and of an undeforming guard ring (2), and on the other hand a deformation detector (5) associated with the diaphragm; the test body (1) is made of an integral piece, in particular plastic, and has a continuous front side (1a) which preferably is planar; the mechanical and dimensional properties of the constituent plastic are matched in such a manner that under the maximum pressure of 30 kilopascals, the diaphragm deflection is within a predetermined range; within this range, the dura mater pressed by the sensor transmits faithfully the intracranial pressure with adequate sensitivity to employ a resistive type transducer which simultaneously is simple, rugged compact and economical.

8 Claims, 2 Drawing Sheets

IMPLANTABLE, INTRACRANIAL-PRESSURE SENSOR

The invention relates to a pressure sensor for implantation in the cranial cavity for transmitting an electrical signal representing the intracranial pressure (hydrostatic pressure of the intraventicular cephalorachitic pressure).

BACKGROUND AND OBJECTS OF THE INVENTION

It is known that knowledge of the intracranial pressure is extremely valuable in many cases in order to monitor and control the clinical condition of a patient (cranial trauma, hydrocephaly, large intracranial lesions ...). Presently there are essentially three types of intracranial-pressure sensors:
- (a) the sensors requiring handling of the cephalorachitic intraventricular liquid or cisternal liquid,
- (b) the so-called sub-dural sensors to be implanted in the subdural space between the dura mater and the arachnoid,
- (c) the extra-dural sensors to be implanted on the dura mater between this dura mater and the skull.

The sensors of the first type (a) measure directly the pressure of the cephalorachitic liquid which is transmitted by a catheter to a transducer. The sensors of the second type (b) measure the intracranial pressure by using the arachnoid as an interface, the arachnoid being a very fine and very flexible membrane capable of integrally transmitting the pressures. In both cases the pressure to be measured is directly accessible, without there being distortions, whereby the measurement provides significant information without need for special precautions and while making use of conventional pressure sensors which are merely selected to have the required sensitivity.

However implanting the sensors (a) or (b) entails effraction of the dura mater necessitating a far more complex surgical intervention than that required by an extradural implant (c) and carries risks (parenchymal lesions, meningitis, fistule of the cephalorachitic liquid ...) well known to the practitioners; in particular, only the extradural implant is suitable for danger-free, long-term surveillance.

The extradural sensors (c) measure the intracranial pressure indirectly by using the dura mater as the interface; in the light of the advantages of this technique (ease of implantation, possibility of long-term implants, patient-risk suppression ...) many sensors of this type have been designed and illustrative examples can be found in the following documents: French Pat. Nos. 2,455,735; 2,384,482; 2,274,261 and 2,262,953; U.S. Pat. Nos. 4,246,908; 4,393,878 and 4,186,749; German Pat. No. 1,965,231.

However control tests have shown that most of the sensors of the type (c) provide spurious outputs without there being an accurate correlation between the measured value and the actual pressure of the cephalorachitic liquid (especially when going from one individual to another). Nevertheless one set of sensors of this type does offer significant measurement values in practice: these are the compensated sensors as described in particular in the French Pat. Nos. 2,455,735 and 2,384,482; the U.S. Pat. No. 4,393,878 and the German Pat. No. 1 965 231. In these latter sensors, a diaphragm is pressed against the dura mater to receive the pressure transmitted by the dura mater on one of its sides, while a compensating system applies a counter-pressure to the opposite side of the diaphragm, this counter-pressure being controlled so as to constantly return the diaphragm to its initial position; the measured parameter is the value of the needed counter-pressure. Such a system results in an exceedingly complex sensor which even when utilizing the most recent technologies cannot be wholly implanted.

In addition, the U.S. Pat. No. 4,186,749 describes a sensor free of the drawbacks attaching to the balanced sensors while still providing meaningful measurements. In this sensor the pressure sensitive diaphragm is metallic with very minute deformations. The main drawback of this sensor is being of low sensitivity and requiring a very sophisticated electronic transducer, whereby its cost is much increased and its bulk is substantial in height, thereby practically making it impossible to place this sensor between the dura mater and the skull. If such a sensor is directly lowered into and placed in the trepan hole, very serious practical difficulties are met in assuring a stable and satisfactory contact with the dura mater; also, it must be anchored on the skull to stay in place.

Accordingly at present there are no extradural implantable sensors providing accurate intracranial pressure information while being simple, whereby they would be economical and offer a bulk compatible with easy and total implantation in the skull between the skull and the dura mater.

The object of the present invention is to remedy this deficiency and to provide a simple sensor which can be easily and extradurally implanted while assuring satisfactory and stable contact with the dura mater, and which furthermore is capable of transmitting an accurate electrical signal representing the intracranial pressure of any individual with an error margin remaining within the bounds generally tolerated by the practitioners (about 5%).

It should be noted that the sensor which is the object of the invention is especially significant when implanted extradurally in the light of the above discussed advantages of this method; nevertheless the geometry of this sensor also is compatible with other implanting modes.

DESCRIPTION OF THE INVENTION

The type of sensor which is the object of the present invention comprises:
- a test body provided with a deforming diaphragm supported at its periphery by an essentially undeforming guard ring,
- a deformation detector associated with the diaphragm and designed to emit an electric signal which is a function of the deformations of said diaphragm,
- and leads attached to the detector to transmit the electrical signal.

In the present invention, said sensor is characterized in that:
- the test body composed of diaphragm and guard-ring comprises an integral assembly of a non-magnetic material so that the peripheral part is the guard ring with a thickness suitable to be essentially undeforming and furthermore that the central part is the diaphragm of lesser thickness,
- the test body has a continuous front side called the transducing side, extending both to the central part comprising the diaphragm and to its peripheral part comprising the guard ring, with a cavity to the rear of the diaphragm providing the thinning at the side diaphragm, the elastic mechanical properties of the test-body substance and the dimensional properties of its central part are so matched that in each cross-section of the diaphragm its maximum deflection with respect to the length of the diaphragm in this cross-section be within 0.01 and 0.03 when the diaphragm is subjected to a uniform relative pressure of 30 kilopascals, the deformation detector includes a strain gauge applied to the inside of the above cavity on that side of the diaphragm which is opposite the transducing side.

The expression "relative pressure" denotes in a conventional manner the difference between the pressures applied to the two sides of the diaphragm.

The term "cross-section" of the diaphragm denotes a plane which is orthogonal to the median plane of the diaphragm.

The above discussed sensor geometry was designed on the basis of research with a large number of dura mater samples whereby it was learned why there was no correlation in most known extradural sensors (except for the balanced ones); there appear to be essentially three reasons.

One reason found by this research is that beyond a critical threshold deformation, the dura mater brings about a change in the transmitted pressure; the deformation-pressure relation is non-linear and depends on the particular dura mater. Under those conditions the pressure picked up by a sensor applied to the dura mater cannot be significantly related to the intracranial pressure the dura mater is subjected to a deformation beyond the critical pressure when threshold cited above. The inventors have determined the value of this critical threshold for the maximum intracranial pressures likely to be found in practice (namely 30 kilopascals). Related to the diaphragm length, this threshold is 0.03. Also the inventors have shown that it is possible when remaining below this threshhold to work with a sufficiently sensitive diaphragm so that its deformations be satisfactorily detected by a plain strain gauge applied on the diaphragm. To that end the diaphragm is selected in such a manner that at the maximum pressure of 30 kilopascals, its deflection related to its length shall exceed the limit value of 0.01.

Accordingly, on one hand, the test body applied against the dura mater will limit its deformations in such a way that the measurements accurately reflect the intracranial pressure over the entire range of pressures met with, and on the other hand the transducer is limited to a mere and very rugged strain gauge of low cost and low bulk. In this manner a sensor is achieved with a very simple geometry, great ease of implantation by simple slipping it between the dura mater and the skull, and with good properties of sensitivity and accuracy.

The second reason for the errors noted in most known sensors arises from practical difficulties in ensuring good contact between the diaphragm and the dura mater, in spite of the screw-anchoring in the skull which most of these sensors require. On the other hand, the sensor of the invention by its very geometry can be made quite thin and its flat shape allows slipping it between the skull and the dura mater while assuring satisfactory and stable contact with this dura mater, without screw and without anchoring.

In particular, the sensor of the invention can be designed in the following manner:

the test body is made of a biocompatible plastic transparent to X-rays and with a Poisson coefficient essentially between 0.30 and 0.45 and a Young's modulus essentially between 2.3 and 2.8 gigapascals, the central part of the test body comprising the diaphragm is essentially between 0.15 and 0.30 mm thick.

In particular the test body may be made by molding or machining one of the following plastics: polycarbonate, methyl polymethacrylate.

Another reason for the lack of accuracy of the known extradural sensors is their structure and their manufacture. In these sensors, the diaphragm as a rule is attached to the guard ring which holds it (by bonding or other fastening means); under these conditions there inevitably is a discontinuity between the diaphragm's tranducing surface and the guard-ring surface, and, in the course of the implantation, mechanical biases are set up and cause errors. In the sensor of the invention, the diaphragm and the guard ring are integrally of the same material and the front transducing side (which is to be applied against the dura mater) extends continuously over the entire surface of the sensor without there being any discontinuity in the radius of curvature at any point of this side.

In a preferred embodiment, this continuous transducing side is planar. In that case the central part comprising the diaphragm and the peripheral surface part comprising the guard-ring then will be co-planar.

The strain gauge which is associated with the diaphragm for delivering an electrical signal as a function of its deformation, may in a known manner include four electrical resistors arranged in two half-bridges and connected to six leads issuing from the test body. In this manner a technically very simple sensor is obtained which is perfectly suited for intra-cranial implantation. The conductors may be made to pass below the scalp to be connected to a power source which may or may not be implanted itself.

DESCRIPTION OF THE DRAWINGS

The description below relating to the attached drawings illustrates in non-restrictive manner an embodiment mode of the invention.

DESCRIPTION OF THE PREFERRED EMBODIMENTS

Figure 1:
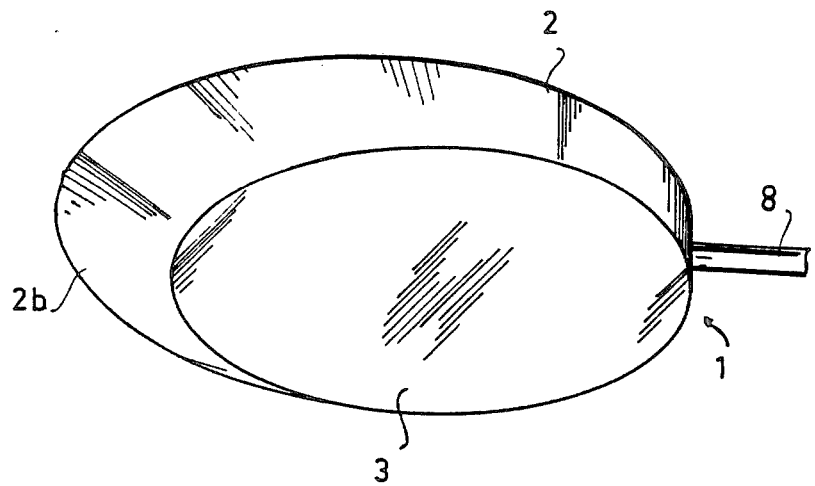
FIG. 1 is an outer perspective shown on an enlarged scale of an intra-cranial pressure sensor of the invention.
Figure 2:
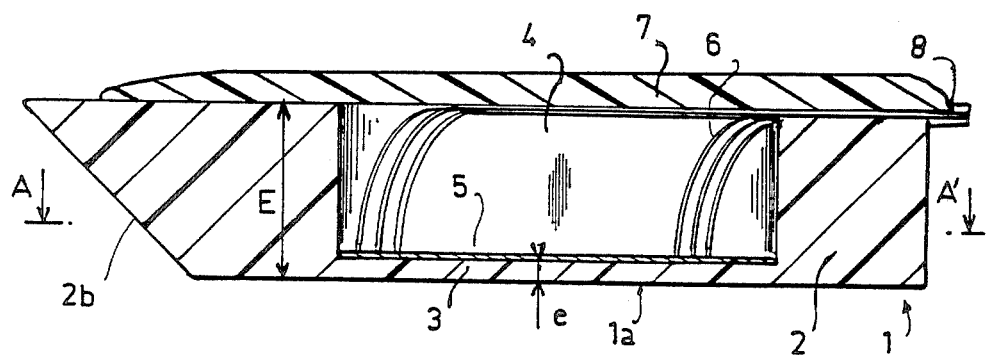
FIG. 2 is a section through a plane Pc orthogonal to the median plane in which extends the sensor.
Figure 3:
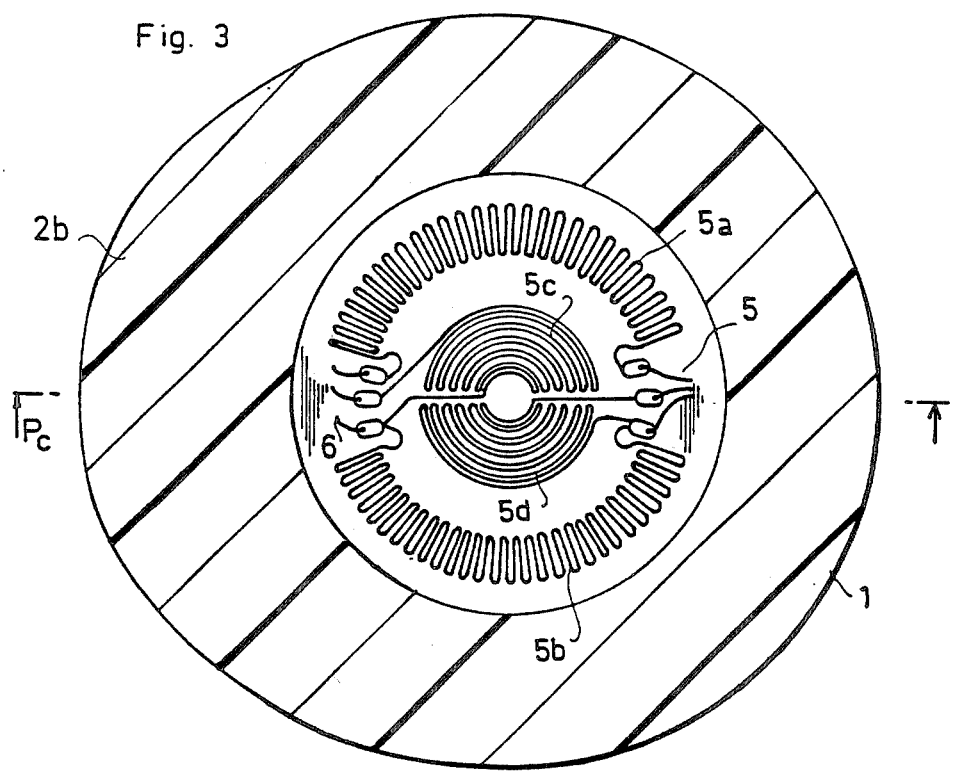
FIG. 3 is a section in a plane AA' parallel to this median plane.

The pressure sensor illustratively shown in the drawings is intended to be implanted against the dura mater between it and the skull in order to emit an electrical signal representative of the hydrostatic pressure of the cephalorachitic liquid applied against the dura mater.

This sensor includes an integral test-body 1 made of one piece by molding methyl polymethacrylate. This material was conditioned during molding with benzoyl peroxide and offers good properties regarding biocompatibility, non-magnetism and X-ray transparency. Its Poisson coefficient is 0.4 and its Young's modulus is 2.46 gigapascals.

The test body 1 includes on one hand a peripheral part 2 with a thickness E between 1 and 3 mm, in particular about 2 mm, whereby its deformations are negligible, and on the other hand a circular central part 3 of which the thickness e is between 0.15 and 0.30 mm, in particular uniformly about 0.25 mm. Therefore the peripheral part acts as a guard-ring for the central part acting as a deforming diaphragm.

The sensor front side will be applied against the dura mater in implantation and shall be termed the "transducing side".

The test body 1 is made by means of a precision-ground flat-bottom mold so that this side is continuous and planar both at the diaphragm 3 and at the guard ring 2. In other words, the front side of the guard ring and the front side of the diaphragm are in the same plane without any discontinuity between them.

In this example, the guard ring 2 extends from the transducing side to the opposite side so as to subtend a slanted sidewall 2b designed to easily insert the sensor between the skull and the dura mater during implantation.

At the rear of the thinner diaphragm, the test body 1 is provided with a cylindrical cavity 4 about 5 mm in diameter.

Figure 4:
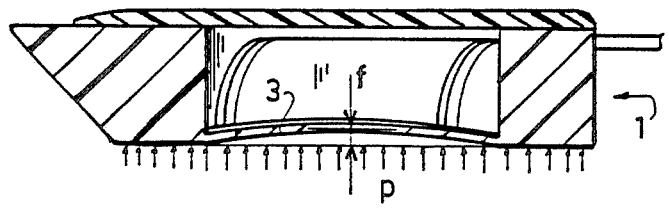
FIG. 4 is a didactic schematic showing the diaphragm deformation in much exaggerated manner.

The elastic properties of the material used and the thickness selected for the diaphragm limit its deformations. Therefore, as schematically shown in FIG. 4, when the sensor is subjected to a relative and uniform pressure of 30 kilopascals, the deflection f in each cross-sectional plane Pc orthogonal to the plane of the diaphragm is about 0.013 relative to the radius of said diaphragm (which is its length in the cross-sectional plane).

The relative intra-cranial pressure always being less than 30 kilopascals (the magnitude of 27 kilopascals being generally considered maximum), the steps discussed above assure that once in place, the diaphragm will be subjected to deformations always less than the critical threshold and below which the dura mater does not appreciably cause distortion of the transmission of the cephalo-rachitic liquid. It should be borne in mind that the research performed by the inventors has shown this threshold to be about 0.030 (maximum deflection related to the unit of length in each sectional plane Pc).

As regards the strain gauge 5, it is bonded in the cavity 4 to the diaphragm side opposite the transducing side. The deformations of the above-described diaphragm are large enough to be detected in a wholly satisfactory manner by such a strain gauge.

This strain gauge includes two peripheral and mutually opposite resistors 5a and 5b meandering along two arcs of a circle near the diaphragm edge. It also includes two other central resistors 5c and 5d arranged as half-coils near the diaphragm center and opposite one another. The peripheral resistors 5a, 5b preferentially detect the radial deformations, which are a maximum at the edge, while the central resistors 5c, 5d preferentially detect the tangential deformations which are a maximum at the center.

These resistors are connected at six points to six leads such as 6 whereby they may be mounted in conventional manner in two half-bridges and with insertion if called for of a thermal compensation means. It should be noted that the strain gauge 5 may be known per se and be of a self-compensating type which thereby would eliminate the need for thermal compensation.

The adhesive used in the example to bond the strain gauge to the diaphragm is methyl-2-cyanoacrylate.

The cavity 4 of the test body is sealed by a coverdisk 7 leaving a free volume at the rear of the diaphragm to allow it to deform. This cover disk comprises a methyl polymethacrylate wall bonded at the edge to the guard-ring. The leads 6 issue from the test body opposite the slanted sidewall 2b. These leads pass between the guard ring and the cover disk 7 and are protected on the outside by a sheath 8 as far as the connector (not shown).

Preferably the cover disk 7 is impermeable and insulates the cavity 4 (in which case the diaphragm determines a slight excess pressure in this cavity). Also it is possible to provide a duct passing from the cavity 4 to the ambient air.

Figure 5:
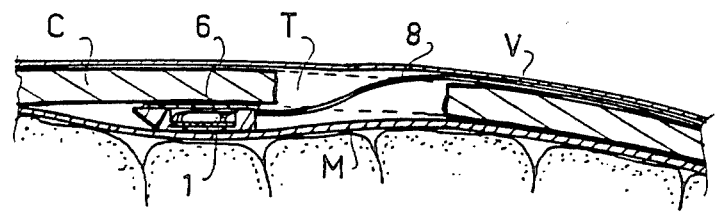
FIG. 5 illustrates the implanted sensor.

FIG. 5 shows an extradurally implanted sensor of the invention. A trepan hole T is made in the skull C to permit inserting the sensor so it will be against the dura mater M; thereupon the sensor is pushed in between the skull and the dura mater M so that its transducing side shall remain applied against the dura mater. The sheath 8 holding the leads 6 leaves through the trepan hole T and passes underneath the scalp V.

In vivo tests performed on dogs of whom the intra-cranial pressure was varied by means of an inflatable balloon implanted within the skull have shown that the measurements faithfully render the hydrostatic pressure of the cephalorachitic liquid with a relative error less than 5%.

It should be noted that the non-magnetic and X-ray transparent test body 1 avoids the appearance of artifacts when analyzing by tomodensitometry or by MRI ("magnetic resonance imaging").

We claim:

1. An implantable intracranial pressure sensor comprising a unitary body member (1) having a central deformable diaphragm portion (3) supported at its periphery by an integral, essentially undeformable guard ring portion (2), said body member being of a non-magnetic material and said guard ring portion being of a greater thickness than said diaphragm portion, so as to define a cavity bounded by said guard-ring portion and said diaphragm portion, said body having a continuous transducing side defined by said diaphragm portion and said guard-ring portion cover means secured to said body member for sealing said cavity opposite said diaphragm portion, a deformation detector (5) within said cavity and associated with said diaphragm for emitting an electrical signal as a function of the deformation of said diaphragm, a plurality of leads connected to said detector for transmitting said electrical signal, said non-magnetic material having mechanical properties of elasticity matched with the dimensional properties of said diaphragm portion such that in each sectional plane of said diaphragm portion, the maximum deflection of said diaphragm portion relative to the length thereof in said plane upon application of a uniform relative pressure of 30 kilopascals is between 0.01 and 0.03, and said deformation detector comprising a strain gauge (5) applied against said diaphragm and within said cavity.

2. An intracranial pressure sensor as in claim 1 and wherein:

said body member is made of a synthetic biocompatible, X-ray transparent material having a Poisson coefficient substantially between 0.30 and 0.45 and a Young's modulus substantially between 2.3 and 2.8 gigapascals, said diaphragm portion having a thickness substantially between 0.15 and 0.30 mm.

3. An intracranial pressure sensor as in claim 2, and wherein said guard-ring portion has a thickness of between 1 and 3 mm.

4. An intracranial pressure sensor as in claim 1 and wherein the surface of said diaphragm portion opposite said cavity and an outer surface of said guard ring portion form said transducing side and lie in a common plane.

5. An intracranial pressure sensor as in claim 1 and wherein said strain gauge includes 4 electrical resistors ($5a$, $5b$, $5c$, $5d$) mounted in half-bridges and connected to six of said leads, said leads extending from said body member.

6. An intracranial pressure sensor as in claim 5 and wherein said diaphragm has a circular shape, and two of said resistors ($5a$, $5b$) are positioned diametrically opposite and arranged along two arcs of a circle near the edge of said diaphragm in such a manner as to preferentially detect radial deformations, and the other two of said resistors ($5c$, $5d$) are arranged near the center of said diaphragm and opposite one another so as to preferentially detect tangential deformations.

7. A pressure sensor as in claim 1 and wherein said non-magnetic material comprises polycarbonate or methyl polymethacrylate.

8. A pressure sensor as in claim 1 and wherein said leads extend from one side of said body member through protective sheath means to connecting pin means, and wherein a peripheral part (2) of said body member opposite said one side is slanted so as to facilitate its insertion during implantation.

* * * * *